(12) United States Patent
Uttenthal

(10) Patent No.: US 7,211,396 B2
(45) Date of Patent: May 1, 2007

(54) ANTIBODY PAIRS AND KITS FOR IMMUNOCHEMICAL DETERMINATION OF MANNAN-BINDING LECTIN

(75) Inventor: Lars Otto Uttenthal, Copenhagen East (DK)

(73) Assignee: AntibodyShop A/S, Copenhagen S (DK)

( * ) Notice: Subject to any disclaimer, the term of this patent is extended or adjusted under 35 U.S.C. 154(b) by 216 days.

(21) Appl. No.: 10/170,317

(22) Filed: Jun. 12, 2002

(65) Prior Publication Data

US 2003/0198998 A1 Oct. 23, 2003

Related U.S. Application Data

(60) Provisional application No. 60/373,754, filed on Apr. 18, 2002.

(51) Int. Cl.
G01N 33/53 (2006.01)
(52) U.S. Cl. .................. 435/7.1; 435/960; 435/975; 435/810
(58) Field of Classification Search ............ 530/388.25; 424/145.1; 435/7.1, 810, 960, 975
See application file for complete search history.

(56) References Cited

U.S. PATENT DOCUMENTS 4,281,061 A * 7/1981 Zuk et al.
6,159,748 A * 12/2000 Hechinger ................. 435/6
6,214,333 B1 * 4/2001 Zoldhelyi et al. .......... 424/93.1

FOREIGN PATENT DOCUMENTS

WO WO 2000/069894 11/2000
WO WO 2002/05833 A1 1/2002

OTHER PUBLICATIONS

Petersen et al. Control of the classical and the MBL pathway of complement activation. Mol Immunol. Oct. 2000;37(14):803-11.*
Campbell A, General properties and applications of monoclonal antibodies, Elsevier Science Publishers, section 1.1, pp. 1-32, 1984.*
ANTIBODYSHOP, Invoice No. 100043, Jun. 14, 2001, Attachment 4, p. 1.*
ANTIBODYSHOP, Invoice No. 100162, Jun. 14, 2001, Attachment 5, p. 1.*
AntibodyShop product specification of HYB 131-01, attachment 1, p. 1, 2005.*
AntibodyShop product specification of HYB 131-10, attachment 2, p. 1, 2005.*
AntibodyShop product specification of HYB 131-11, attachment 3, p. 1, 2005.*
Steffensen R. et al., "Detection of structural gene mutations and promoter polymorphisms in the mannan-binding lectin (MBL) gene by polymerase chain reaction with sequence-specific primers", J. Immunological Methods 2000 241:33-42.
Hansen et al., "Purification and Characterization of Two Mannan-Binding Lectins from Mouse Serum", J. Immunology 2000 164:2610-2618.
Koch et al., "Immunochemical detection and quantification of abnormal forms of mannan-binding lectin in human serum and plasma", INTERLEC 20, The Twentieth International Lectin Meeting 2002 Copenhagen, Denmark.
Lipscombe et al., "Distinct physicochemical characteristics of human mannose binding protein expressed by individuals of differing genotype", Immunology 1995 85(4) :660-667.
Kurata et al., "Role of the Collagen-Like Domain of the Human Serum Mannan-Binding Protein in the Activation of Complement and the Secretion of this Lectin", Biochemical and Biophysical Research Communications 1993 191(3) :1204-1210.
Terai et al., "Relationship between gene polymorphisms of mannose-binding lectin (MBL) and two molecular forms of MBL", Eur. J. Immunol. 2003 33:2755-2763.
Zimmermann-Nielsen et al., "Complement Activation Mediated by Mannan-Binding Lectin in Plasma from Healthy Individuals and from Patients with SLE, Crohn's Disease and Colorectal Cancer. Suppressed Activation by SLE Plasma", Scand. J. Immunol. 2002 55:105-110.
Website Reference: "HBT Elisa Test Kit for Human MBL (Lectin assay)", HyCult Biotechnolgy b.v. Oct. 2002.
Website Reference: "MBL Oligomer Elisa", AntibodyShop Aug. 2003.

* cited by examiner

*Primary Examiner*—Maher M. Haddad
(74) *Attorney, Agent, or Firm*—Licata & Tyrrell P.C.

(57) ABSTRACT

Various antibodies with different binding characteristics for MBL A or MBL B bound to mannan or MBL A or MBL B bound to an antibody against MBL are provided. Also provided are methods for selecting antibodies against MBL with different binding characteristics and methods and kits for using these antibodies to measure MBL capable of binding to mannan or oligomerized MBL and abnormal, poorly oligomerized MBL in a sample. The methods and kits are useful in diagnosing increased susceptibility to and exacerbation of infections and autoimmune diseases.

7 Claims, No Drawings

US 7,211,396 B2

ANTIBODY PAIRS AND KITS FOR IMMUNOCHEMICAL DETERMINATION OF MANNAN-BINDING LECTIN

INTRODUCTION

This application claims the benefit of priority from U.S. Provisional Patent Application No. 60/373,754, filed Apr. 18, 2002, which is herein incorporated by reference in its entirety.

FIELD OF THE INVENTION

Mannan-binding lectin (MBL) can exist in different amounts and in different genetically determined variant forms in different individuals thereby influencing the susceptibility of these individuals to infectious and autoimmune diseases. The present invention provides a series of monoclonal antibodies against human mannan-binding lectin (MBL) that are useful in quantifying concentrations of this protein, particularly in biological fluids such as human serum or plasma, and in providing structural and functional information about the protein. In one embodiment of the present invention, compositions, methods and kits are provided for measuring oligomerized MBL capable of binding to mannan. In another embodiment, compositions, methods and kits are provided for measuring total immunoreactive MBL subunits, whether or not these are oligomerized into the pentamer or hexamer structures that characterize MBL of full biological activity. The compositions, methods and kits of the present invention are useful in the field of biochemistry and medicine.

BACKGROUND OF THE INVENTION

Mannan-binding lectin (MBL) is an important component of the innate immune system. It is a multimeric protein synthesized in the liver and is one of the C-type lectins, showing calcium-dependent binding to certain carbohydrate (polysaccharide) structures on the surface of microorganisms. Mannan is used as a model of such polysaccharides and MBL shows affinity for monosaccharide components such as N-acetyl-glucosamine and D-mannose. Upon binding to microbial polysaccharides, MBL activates complement by means of associated serine proteases known as MASP-1, MASP-2 and MASP-3, and promotes killing of the microorganism by means of the lytic membrane attack complex and phagocytosis by its opsonizing effect and by direct interaction with putative cell surface receptors.

The MBL molecule is an oligomeric complex of up to six sets of homotrimers of a single chain of 228 amino acid residues. Each chain consists of a 20 amino acid N-terminal cysteine-rich domain followed by a collagen-like domain of 18–20 Gly-Xxx-Yyy repeats, an alpha-helical coiled-coil neck region, and finally, a carbohydrate recognition domain (CRD). Three of these chains form a structural unit or "head", in which the collagen domains form a triple helix ending in three neck regions that each bears a CRD. The N-terminal domains are linked by interchain disulfide bonds. Up to six such homotrimer heads are then linked via their N-terminal regions to form the structure of the normal MBL molecule, which has been compared to a bunch of three-petalled flowers. This structure is maintained by the formation of disulfide bonds between individual chains of the linked homotrimers. In this form, MBL is capable of associating with the serine proteases MASP-1, MASP-2 and MASP-3 (and with a related non-enzymatic peptide known as MAp19), this complex being capable of activating complement when MBL binds to carbohydrate.

The human MBL gene (mbl2) shows a number of allelic variants. Some occur in the promoter region, the two most significant occurring at positions −550 (H or L) and −221 (Y or X); a further variant occurs in the 5'-untranslated region at position +4 (P or Q); and three occur in exon 1, at position +223 (A or D, Arg52Cys), +230 (A or B, Gly54Asp) and +239 (A or C, Gly57Glu). The promoter haplotypes HY, LY and LX are associated with high, medium and low plasma levels of MBL, respectively, whereas the haplotypes of exon 1 affect the structure and association of the protein chains. Linkage disequilibrium determines that some of the theoretically possible MBL haplotypes are extremely rare and have not been found; among 100 Danish blood donors only the following haplotypes were detected (frequency in brackets): HYPA (0.285), LYQA (0.235), LXPA (0.195), LYPB (0.135), HYPD (0.085), LYPA (0.045), LYQC (0.020). Among A/A genotypes (i.e. with a normal collagenous region), only the LXP/LXP genotypes showed low plasma MBL levels. A/B, A/C and A/D genotypes (i.e. heterozygous for normal and abnormal collagenous regions) showed reduced plasma MBL levels as determined by the old method described; when this was combined with an LX haplotype, even lower levels were recorded. B/B, C/D and D/D genotypes (i.e. with an anomaly of all collagenous regions) showed very low levels of MBL as determined by the old method, even though none of these subjects showed an LX haplotype. The frequencies of the exon 1 haplotypes A, B, C and D in the Danish donors were 0.76, 0.135, 0.020 and 0.085, respectively. This means that the frequencies of A/A, B/B, C/C and D/D genotypes will be the square of these, i.e. affecting 58.76%, 1.82%, 0.04% and 0.72% of the population, respectively (data from Steffensen, R. et al. (2000) J Immunol Methods 241:33–42).

Possible structures of human MBL from B/B, C/C and D/D genotypes have been determined by analyzing the corresponding recombinant proteins expressed in Chinese hamster ovary cells. The results are similar for these three genotypes, and are described with reference to the B/B genotype, responsible for the commonest severe structural abnormality of MBL. Analysis of unreduced MBL from this genotype (known as MBL B) shows that it occurs principally as dimers of two chains, and three such dimers may be linked to form a structure corresponding to two triplet "heads" of normal MBL from A/A genotypes (known as MBL A). Higher oligomers are not formed, and MBL B, whether recombinant or prepared from human donors, associates less strongly with the MASPs, so that it fails to activate complement in in vitro tests.

A/B heterozygotes are believed to possess a mixture of MBL A and B single chains that combine in various ways. Because normal MBL contains up to 18 single chains in six trimeric heads, the proportion of such molecules consisting entirely of normal MBL A chains will be very small in the A/B heterozygotes. The effect of the theoretical 50% admixture of MBL B chains will therefore be to disrupt the structure of the vast majority of the MBL oligomers, so that the B trait is dominant in terms of the MBL phenotype, i.e. the majority of the MBL adopts a structure similar to that of MBL B. The same consideration applies to A/C and A/D heterozygotes, although it appears that the disruptive effect of D chains may be somewhat less than that of B chains.

Existing methods of measuring human MBL depend on the use, in a variety immunoassay designs, of polyclonal and/or monoclonal antibodies raised against MBL. In many cases it is not clear which molecular forms of MBL are preferentially measured by these methods. One commonly used method depends on the use of the mouse monoclonal antibody HYB 131-01 raised against purified human MBL as both capture and detection antibodies in a sandwich ELISA (enzyme-linked immunosorbent assay). In this procedure HYB 131-01 is coated onto microtiter wells so that it can bind MBL in human serum or plasma samples. The amount of MBL bound is a function of the concentration of MBL in the samples. Bound MBL is then quantified by adding labeled HYB 131-01 as a detection antibody. The label can be an enzyme, such as horseradish peroxidase or alkaline phosphatase, capable of producing a quantitative color reaction when incubated with a suitable substrate, or it can be biotin, capable of binding avidin or streptavidin complexed with a suitable enzyme, or it can be europium, to allow detection by time-resolved fluorescence.

These methods also depend on two identical antibody molecules (one to capture and one to detect) binding to a single MBL molecule at two identical but separate sites (epitopes). In practice, this only takes place when the MBL molecule is an oligomer of trimeric subunits, so that only MBL oligomers are measured by these assays. Single or poorly oligomerized MBL trimeric subunits will not permit the simultaneous binding of both capture and detection antibodies. In consequence, these methods cannot adequately measure MBL that is poorly oligomerized, nor can they determine whether the MBL oligomers measured are in fact capable of binding to mannan, one of the defining characteristics of functional MBL. Existing assay methods for determining serum or plasma concentrations of MBL are also incapable of determining whether a low recorded concentration of MBL is due to a low concentration of normal MBL A, as in the LXPA/LXPA genotype, or due to MBL of anomalous structure that does not react adequately in the assay, as in the A/B, A/C, A/D, B/B C/D and D/D genotypes.

However, it is desirable to distinguish between low concentrations in plasma of MBL A and low recorded concentrations that are in fact due to the presence of normal or near-normal concentrations of MBL B, C and D variants. For example, MBL B has been reported to have the same cell-mediated cytotoxic, opsonic and phagocytosis-promoting activities as MBL A. Thus, the failure of the existing assay method to detect MBL B does not reflect these functions of this MBL. In addition, both low plasma concentrations of MBL, as measured by existing immunoassays, and promoter or exon 1 allelic forms associated with such low concentrations, have been correlated with an increased risk of infection in childhood and in immunocompromised patients. They are also correlated with disease progression in chronic granulomatous disease and cystic fibrosis, and with a more severe course of autoimmune diseases such as systemic lupus erythematosus and rheumatoid arthritis. As the existing assays have only been able to give a partial picture of a patient's MBL status, it is expected that more precise correlations could be obtained with more differentiated analyses of this status.

SUMMARY OF THE INVENTION

An object of the present invention is to provide methods for selecting monoclonal antibodies raised against MBL based upon their ability to bind or not to bind to MBL A bound to mannan or MBL B bound to mannan.

Another object of the present invention is to provide methods for selecting monoclonal antibodies raised against MBL based upon their ability to bind or not to bind to MBL A bound to the same or a different monoclonal antibody against MBL or to MBL B bound to the same or a different monoclonal antibody against MBL.

Another object of the present invention is to provide antibodies raised against MBL and which have the ability to:
 (a) bind or not bind to MBL A bound to mannan;
 (b) bind or not bind to MBL B bound to mannan;
 (c) bind or not bind to MBL A bound to the same or a different monoclonal antibody raised against MBL; or
 (d) bind or not bind to MBL B bound to the same or a different monoclonal antibody raised against MBL, with the proviso that the antibody is not HYB 131-01.

Another object of the present invention is to provide in vitro methods and kits for measuring MBL that is capable of binding to mannan in a sample.

Another object of the present invention is to provide in vitro methods and kits for measuring normal oligomerized MBL and abnormal, poorly oligomerized MBL in a sample.

The methods, kits and antibodies of the present invention are useful in diagnosing increased susceptibility to and exacerbation of infections and autoimmune diseases by measuring MBL in human plasma or serum samples that is capable of binding to mannan or by measuring MBL in human plasma or serum samples by a method that is capable measuring both normal oligomerized MBL and abnormal, poorly oligomerized MBL.

DETAILED DESCRIPTION OF THE INVENTION

The present invention provides antibodies other than HYB 131-01, methods for selecting antibodies other than HYB 131-01, and methods and kits for using antibodies in in vitro methods for measuring mannan-binding lectin (MBL) concentrations in samples. Using the antibodies, methods and kits of the present invention, the presence of variant forms of MBL can be distinguished from the presence of low concentrations of normal MBL. In addition, total amounts of MBL can be measured independently of the state of oligomerization of MBL and compared with oligomerized MBL capable of binding strongly to mannan.

The antibodies, methods and kits of the present invention are particularly useful in quantifying and characterizing MBL in samples comprising biological fluids, particularly human serum and plasma. When using the assay to analyze for the capacity of MBL to bind to mannan in plasma samples, it is preferred that the blood sample be anticoagulated with heparin as opposed to chelators of calcium such as citrate or EDTA because the binding of MBL to mannan depends on the presence of free ionized calcium. If only plasma anticoagulated with calcium chelator is available, an excess of calcium salt must be added to saturate the chelator and ensure a physiological concentration of free ionized calcium in the presence of the chelator.

One aspect of the present invention relates to methods for selecting monoclonal antibodies raised against MBL with different binding capabilities. In one embodiment of this method, monoclonal antibodies raised against MBL are selected based upon the ability of the monoclonal antibody to bind or not to bind to MBL A when bound to mannan. In this embodiment, monoclonal antibodies are also selected based upon their ability to bind or not to bind to MBL B when bound to mannan. In another embodiment of this method, monoclonal antibodies raised against MBL are selected based upon their ability to bind or not to bind to MBL A when bound to the same or a different monoclonal antibody against MBL. In this embodiment, antibodies are also selected based upon their ability to bind or not bind to MBL B when bound to the same or a different monoclonal antibody against MBL. Using these selection methods, antibodies raised against MBL and which have the ability to bind or not bind to MBL A bound to mannan; bind or not bind to MBL B bound to mannan; bind or not bind to MBL A bound to the same or a different monoclonal antibody raised against MBL; or bind or not bind to MBL B bound to the same or a different monoclonal antibody raised against MBL were identified.

Thus, another aspect of the present invention relates to antibodies other than HYB 131-01 raised against MBL which have the ability to either bind or not bind to MBL A when bound to mannan, bind or not bind to MBL B when bound to mannan, bind or not bind to MBL A when bound to the same or a different monoclonal antibody raised against MBL, or bind or not bind to MBL B when bound to the same or a different monoclonal antibody raised against MBL.

Antibodies of the present invention were prepared and characterized as follows.

Human MBL for use as the immunogen was purified from plasma from blood donors. Prior to purification, each portion of blood was screened for HBsAg, and antibodies against HIV 1 and 2 and HCV. MBL was isolated by affinity chromatography on a carbohydrate column (Sepharose). After the column had been washed with the binding buffer containing calcium chloride at physiological pH, the MBL was eluted with calcium-free buffer containing EDTA. Elution with a calcium-free, calcium chelating buffer at physiological pH is important, as elution by other means, such as the use of non-physiological pH or salts, solutes and solvents that modify the structure of proteins or water, will also elute antibodies such as IgM that are also bound to the carbohydrate column. The eluate was subjected to molecular size chromatography on a Sepharose column, the protein peak emerging near the void volume being collected. This procedure removed the lower molecular weight serum amyloid protein A, which also shows calcium-dependent binding to carbohydrate. The resulting product was concentrated by ultrafiltration, analyzed by sodium dodecyl sulfate-polyacrylamide gel electrophoresis (SDS-PAGE) in the reduced and unreduced state.

The purified MBL was adsorbed to aluminum hydroxide gel and injected intraperitoneally into BALB/c×CF2 female mice in doses of 25 micrograms of adsorbed protein. Techniques for monitoring the immune response and preparing monoclonal antibodies were performed in accordance with techniques well known to those skilled in the art and described in standard reference texts such as Harlow, E. and Lane, D. (1988; Antibodies: A Laboratory Manual. Cold Spring Harbor Laboratory, New York).

Hybridoma supernatants were screened by ELISA performed in microwells coated with purified human MBL. As a result of this screening, new hybridomas coded HYB 131-01b, HYB 131-10 and HYB 131-11 were selected and the corresponding mouse monoclonal antibodies with the same respective codes were further characterized.

Characterization of antibodies of the present invention included comparison with the monoclonal antibody HYB 131-01 used in a previously described assay method. This comparison revealed that four antibodies, HYB 131-01, HYB 131-01b, HYB 131-10 and HYB 131-11, each bound to different respective non-overlapping epitopes on the MBL molecule. Thus, binding of one of these antibodies to MBL did not prevent the simultaneous binding of the other three antibodies to the same MBL. Studies of the relation of these four epitopes to the carbohydrate binding site of the MBL monomer revealed that HYB 131-01 bound close to this site and interfered with the binding of MBL to mannan. Thus, MBL complexed with an excess of antibody HYB 131-01 failed to bind to mannan-coated microwells. In contrast, MBL complexed with an excess of HYB 131-01b, HYB 131-10 or HYB 131-11, still bound to mannan-coated microwells. Thus, from these experiments, it was concluded that the epitopes for antibodies HYB 131-01b, HYB 131-10 or HYB 131-11 did not overlap with the carbohydrate binding site. However, reaction of these antibodies in immunoblots of MBL that had been subjected to digestion with collagenase to remove the collagenous and N-terminal domains indicated that these antibodies, like HYB 131-01, bound to epitopes located in the remaining neck-plus-CRD portion of the molecule.

The reactivity of the monoclonal antibodies was tested against MBL A and MBL B in sera from donors genotyped as A/A and B/B respectively. When MBL A and MBL B were bound to mannan coated onto ELISA microwells at a concentration of 0.3 micrograms per milliliter, antibodies HYB 131-01, HYB-01b, HYB-10 and HYB-11 conjugated with horseradish peroxidase gave an approximately equal reaction with MBL A, but showed no significant reaction with MBL B. Increasing the density of the mannan coat by coating at 5 micrograms per milliliter increased the signal produced by the binding of each antibody to MBL A, suggesting that more MBL A was bound to the coat. It also produced slight changes in the relative binding of the different antibodies to MBL A from a single A/A genotype donor and MBL purified from a serum pool from healthy donors, suggesting that the latter MBL was heterogeneous, containing forms that bound slightly differently to mannan coats of different density and/or to the different antibodies. In no case was binding of antibody to MBL B detected.

It is concluded that when MBL is bound to a mannan coat, the protein is held with its mannan-bound CRDs in such an orientation that none of the tested antibodies can gain access to their epitopes on the bound CRDs. Only oligomerized MBL A with a sufficient number of heads to ensure that some heads are bound to the coat while others are swinging free in the liquid phase will be able to bind the antibodies via its free heads. There are minor differences in reactivity of the four antibodies tested with these postulated free heads. MBL B, with a maximum of two heads or abnormal single heads consisting of two chains, is bound to the mannan coat in such a manner as not to allow any of the antibodies to bind to the CRDs, because there are no unbound CRDs available in the liquid phase. The binding of MBL B to a mannan-coated surface is also weaker than that of MBL A, and other experiments have determined that prolonged incubation is required to obtain efficient binding. This is attributed to the fact that the binding of MBL A to a mannan-coated surface is stabilized by synergy from the binding of multiple heads of the same oligomer to the surface, whereas the binding of MBL B is not subject to the same degree of binding synergy. It is therefore probable that the washing steps of the subsequent assay procedure in fact remove any MBL B bound to the coat, making this procedure highly specific for normally oligomerized MBL.

The reactivities of the four antibodies with MBL A and MBL B were also tested in pair-wise comparisons. In these assays, each purified antibody was used to coat microtiter wells. Dilutions of human sera containing either MBL A or MBL B were then added and the binding to bound MBL of purified, labeled versions of each of the other three antibodies was measured. The concentration of MBL A in serum from a single donor of A/A genotype was determined as 760 ng/ml by means of a previously described assay method using HYB 131-01 both as coat and detection antibody, and MBL purified from pooled donor plasma as a gravimetric standard. Table 1 shows the MBL concentrations obtained with each combination of antibodies for the MBL A serum and the MBL B serum, by comparison with the same standard.

TABLE 1

MBL concentrations in ng/ml, measured by enzyme-linked immunosorbent assay (ELISA) using different combinations of coating and detecting antibodies, in sera containing MBL A and MBL B, respectively. SD: standard deviation; CV: coefficient of variation

| Detecting antibody Coating antibody | HYB 131-01 | | HYB 131-01b | | HYB 131-10 | | HYB 131-11 | | Mean SD CV |
|---|---|---|---|---|---|---|---|---|---|
| | MBL A | MBL B | MBL A | MBL B | MBL A | MBL B | MBL A | MBL B | |
| HYB 131-01 | 760 | | 980 | | 900 | | 870 | | 878 91 10% |
| | | 0 | | 130 | | 140 | | 70 | 85 65 76% |
| HYB 131-01b | 820 | | 840 | | 990 | | 870 | | 880 76 9% |
| | | 50 | | 90 | | 100 | | 210 | 113 68 61% |
| HYB 131-10 | 790 | | 910 | | 920 | | 1040 | | 915 102 11% |
| | | 160 | | 170 | | 190 | | 530 | 263 178 68% |
| HYB 131-11 | 1050 | | 1100 | | 960 | | 790 | | 975 136 14% |
| | | 140 | | 80 | | 180 | | 0 | 100 78 78% |
| Mean | 855 | 88 | 958 | 118 | 943 | 153 | 893 | 203 | |
| SD | 132 | 75 | 111 | 41 | 40 | 41 | 105 | 235 | |
| CV | 15% | 86% | 12% | 35% | 4% | 27% | 12% | 116% | |

In the following text, combinations of coating/detecting antibodies are referred to in that order, using only the final part of the reference number for each antibody; e.g. 01/01b means that HYB 131-01 was used as coat and HYB 131-01b as detecting antibody.

The apparent concentration values obtained for MBL A varied from 760 ng/ml with 01/01 (using the previously described assay) to 1100 ng/ml with 11/01b. Thus, using different combinations of antibodies, up to 45% more MBL A could be detected from this donor than that measured by the previously described assay in comparison with the pooled, purified MBL standard. Neither the MBL in the single donor plasma nor that in the standard is homogeneous, so that an increase in the recorded value for the single donor serum may in part be due to a decreased reactivity of that antibody combination with the pooled standard. The coefficients of variation for MBL A concentrations obtained with different detecting antibodies used in combination with the same coating antibody, and with the same coating antibody used in combination with different detecting antibodies, show that HYB 131-01b as coating antibody binds MBL in such a way as to allow detection with different antibodies with least variation, whereas HYB 131-10 as detecting antibody shows least variation in detecting MBL bound to different coats.

The reliability of HYB 131-10 as a detection antibody that shows little sensitivity to the way in which MBL is presented by different coats was confirmed by testing a larger number of sera from different genotyped donors in microwells coated with mannan at different concentrations. Of the four detecting antibodies, HYB 131-10 gave the most consistent results for MBL from the same serum bound to different mannan coats.

The highest mean values of the MBL A concentration were obtained with HYB 131-11 and HYB 131-10 as coating antibodies, averaging the results obtained with the four detecting antibodies. This suggested that HYB 131-11 and HYB 131-10 had higher affinity for MBL than HYB 131-01b and HYB 131-01.

The differences in recorded MBL A concentrations shown when MBL A bound to the same coat is measured with different detection antibodies suggest that certain coating/detecting pairs of antibodies bind simultaneously to MBL A with greater efficiency than others. It is postulated that, for MBL A, this depends on a combination of factors. The angle at which the different antibodies hold the bound MBL heads depends on the location of their epitopes on the CRD and this affects the degree of accessibility of the other epitopes to their respective antibodies. At the same time the affinity of the individual antibody may affect the result.

The union of the detecting antibody depends in great part on its union to unbound MBL heads swinging out into the liquid phase, the epitopes on coat-bound heads being blocked by binding to the coating antibody. However, as each head has three CRD regions arranged in radial symmetry, some binding of the detection antibody to coat-bound heads may still be possible, if the location of the epitope in question is such that the angle of binding of the triplet head via one or two of these identical epitopes permits access of the detecting antibody to the remaining two or one epitopes on the same head. The extent to which this can occur is shown by the results obtained when the same antibody is used to measure the concentration of MBL B, which has very few or no heads swinging free in the liquid phase. Neither the 01/01 nor the 11/11 combination can measure MBL B, as shown in Table 1. Accordingly, these combinations of the same antibody can only measure oligomerized MBL that has unbound heads exposed to the detecting antibody in the liquid phase.

The combination of 01b/01b antibodies gave a total reading for MBL A of 840 ng/ml. This can be analyzed as follows: reading expected from binding to free heads in the liquid phase=760 ng/ml (the reading from 01/01, which is incapable of binding to coat-bound heads); reading expected from binding to coat-bound heads=90 ng/ml (the reading obtained by 01b/01b for MBL B); total expected reading=850 ng/ml. The agreement between the expected reading (850 ng/ml) and the reading actually found (840 ng/ml) is quite good.

The combination of 10/10 antibodies gave a total reading for MBL A of 920 ng/ml. This can be analyzed as follows: reading expected from binding to free heads in the liquid phase=760 ng/ml (the reading from 01/01, which is incapable of binding to coat-bound heads); reading expected from binding to coat-bound heads=190 ng/ml (the reading obtained by 10/10 for MBL B); total expected reading=950 ng/ml. The agreement between the expected reading (950 ng/ml) and the reading actually found (920 ng/ml) is again quite good.

In both cases the calculations are approximate, as they are based on the assumption that the amount of MBL B in the MBL B serum is comparable to the amount of coat-bound MBL A heads in the MBL-A sample. However, the highest estimate of the MBL B concentration (which is probably the closest approach to reality) is 530 ng/ml, and the proportion 530/760 may not be far from the proportion of coat-bound heads to total heads in the MBL A sample. If anything, it may be somewhat larger than this proportion.

It is assumed that combinations of different antibodies for coating and detection give readings for MBL A as a function of their reaction with non-coat-bound heads plus an additional reaction with coat-bound heads that depends on the accessibility of the detecting antibody to its epitope(s) on these heads. This will depend on the relative positions of the epitope for the coating antibody and that for the detecting antibody, governing the angle between them and the exposure of the epitope for the detecting antibody on the radially symmetrical triplet head once it is bound down to the coat via one or two of the epitopes for the coating antibody. Geometric considerations determine that inverting the use of the antibodies within a pair will not give the same result, i.e. 11/01b gives an MBL A reading of 1100 ng/ml, whereas 01b/11 gives a reading of 870 ng/ml. A further consideration in this respect is that higher readings will in general be obtained if the antibody of higher affinity is used as coat, as the coat and its bound MBL are subjected to more washings than the detection antibody during the assay procedure.

The apparent concentration values obtained for MBL B varied from zero with 01/01 (the previously described assay) and with 11/11, to 530 ng/ml with 10/11. MBL B has normal neck and CR domains and therefore shows the same epitopes for the four antibodies as MBL A. However, MBL B consists of dimers of single MBL chains and hexamers that may be organized into two triplet heads, the maximum number of heads found in an MBL B molecule. It is believed that MBL B is bound to the antibody coating such that all twin and triplet CRD heads are held in contact with the coat via at least one epitope of the two or three identical epitopes for the coating antibody. The angle at which the MBL heads are bound depends on the location of the epitope in question on the CRD and this affects the accessibility of the other epitopes to their respective detecting antibodies, whether the detecting antibody is the same as the coating antibody or a different antibody.

The measurement of MBL B in this system therefore depends almost entirely on the relative positions of the coating and detecting antibody epitopes and the effect of binding to the coat on the exposure of epitopes for the detecting antibody. Neither the 01/01 nor the 11/11 combination can measure MBL B. This indicates that the epitopes for antibodies HYB 131-01 and HYB 131-11 are so positioned on the CRD that binding of a twin or triplet head via a single epitope holds the head in such a position that the other epitope or two epitopes for the same antibody are maintained in a position that is unavailable to the liquid phase. These epitopes may also be bound to the coat. It is concluded that their position on the CRD is such that they point in the same direction when the CRDs are arranged in radial symmetry in the twin or triplet heads.

The combinations 01b/01b and 10/10 are capable of measuring some MBL B. This implies that the epitopes for these antibodies are so positioned on the CRD that they point in different directions when the CRDs are arranged in twin or triplet heads. The fact that 01b/01b gives a reading of 90 ng/ml whereas 10/10 gives a reading of 190 ng/ml may be due to the higher affinity of antibody HYB 131-10, and/or to an influence of epitope position whereby the non-coat-bound epitopes for HYB 131-10 are better exposed to the liquid phase.

Combinations of different antibodies as coating and detecting antibodies are all capable of measuring some MBL B. This is believed to be due to the fact that the four different antibodies all bind to non-overlapping epitopes on the CRD. Thus, there must be some angle between them, and the relative positions and angling of the different epitopes appear to be the major factor governing the reading obtained. Geometric considerations determine that inverting the use of the antibodies within a pair will not give the same result, i.e. 11/01b gives an MBL B reading of 80 ng/ml, whereas 01b/11 gives a reading of 210 ng/ml. The highest reading for MBL B (530 ng/ml) was obtained with 10/11, implying that once MBL B is bound to the HYB 131-10 coat, the epitope for HYB 131-11 is well exposed to this detecting antibody. On theoretical grounds it is assumed that the highest reading of the MBL B concentration obtained from a series of antibody pairs will be closest to the gravimetric concentration, if it were possible to determine the latter.

Thus, the combination of 10/11 antibodies is the most suitable combination of antibodies for measuring MBL B, and by analogy, MBL C and D as well, and for measuring MBL from A/B, A/C and A/D heterozygotes. This combination also gives a high reading of 1040 ng/ml for MBL A, so that it may be suitable for measuring total immunoreactive MBL in a patient sample. Another combination that can be used for measuring total immunoreactive MBL concentrations is 11/01. Plasma MBL concentrations recorded with this combination for blood donors of different MBL genotypes are shown in Table 2, where they are compared with results from the 01/01 combination (the previously described assay) and the 11/11 combination.

Table 2 shows that the readings obtained with 11/01, 01/01 and 11/11 are in reasonable agreement for all A/A genotypes, whether or not these are associated with a promoter defect. For A/B, A/D, B/B and B/D genotypes, 11/01 measures considerably more MBL than the other two antibody combinations, while the 11/11 combination gives intermediate values, except for the B/B genotype. It will be noted that the A/D genotype typically shows only a moderately reduced MBL value even with the previously described assay, in confirmation of previous studies (Steffensen, R. et al. supra). Although recombinant MBL D is similar to recombinant MBL B, D chains appear to be better able than B chains to combine with A chains to form a proportion of MBL of normal or near-normal structure. The 10/11 combination gives a reading for MBL B that is about three-fold higher than that obtained with 11/01. It probable that the 11/01 combination in this study is "under-reading" the MBL in the samples from the B/B and B/D genotypes by a similar factor.

TABLE 2

Plasma MBL concentrations (ng/ml) in blood donors of different MBL genotype, determined with different combinations of antibodies. PD: Promoter defect (genotype) LX/LX or LX/LY

| Antibody combination | | | 01/01 | |
|---|---|---|---|---|
| Donor no. | Genotype | 11/01 | (old assay) | 11/11 |
| 1 | A/A | 1460 | 1460 | 1440 |
| 2 | A/A | 1840 | 2530 | 2330 |
| 3 | A/A | 1520 | 1800 | 1690 |
| 4 | A/A | 2950 | 3990 | 4110 |
| 5 | A/A PD | 510 | 570 | 580 |
| 6 | A/A PD | 360 | 340 | 460 |
| 7 | A/B | 1170 | 350 | 790 |
| 8 | A/B | 2100 | 320 | 880 |
| 9 | A/D | 2140 | 1030 | 1460 |
| 10 | B/B | 570 | 50 | 0 |
| 11 | B/D | 660 | 20 | 220 |
| 12 | B/D | 530 | 20 | 290 |

It is not intended that MBL in samples should be measured by all or many of these different antibody combinations, but that the optimal combination for the measurement of structurally abnormal MBL in addition to structurally normal MBL, up to now the 10/11 combination, should be selected for regular use and values obtained from this assay compared with those obtained in the same assay from dilutions of the best available MBL standard in the form of a serum pool derived from healthy donors. The selection of further monoclonal antibodies against MBL by the procedures of this invention may in future produce other antibody pairings that measure structurally abnormal MBL with even greater efficiency. Assays based on these antibody pairings will then be used with the same standard and replace the 10/11 assay. The choice of the optimal biological standard for a substance as structurally heterogeneous as MBL is problematical and existing heterogeneous standards prepared from pools of sera from healthy donors may be in future be replaced by standards of known structure prepared from recombinant MBL A and recombinant MBL B and other recombinant forms, without affecting the principle of the present invention.

Another aspect of the present invention relates to in vitro methods and kits for measuring MBL that is capable of binding to mannan in a sample or for measuring normal oligomerized MBL and abnormal, poorly oligomerized MBL in a sample. These methods are useful in diagnosing increased susceptibility to and exacerbation of infections and autoimmune diseases.

Any variety of well known immunoassay technologies can be used in the methods of the present invention. For immunoassays of the present invention, it is preferred that MBL capable of binding to mannan or total immunoreactive MBL in a sample be immobilized to a solid phase via a capture molecule such as mannan or an antibody of the present invention, respectively. Immobilized MBL capable of binding to mannan or total immunoreactive MBL in the sample can then be detected via a second antibody of the present invention which is detectably labeled.

In one embodiment, the methods comprise an enzyme linked immunosorbent assay (ELISA) consisting of an ELISA assay kit containing microtiter wells precoated with either mannan or a selected monoclonal antibody against MBL, a solution of a selected monoclonal antibody against MBL, this antibody being detectably labeled, for example with biotin, or with a detectable enzyme or a chromogenic substrate such as alkaline phosphatase, or with europium to permit detection by time-resolved fluorescence emission, solutions of human MBL as standards and controls, and a solution of chromogenic substrate for the enzyme used. In the case of biotin-labeled antibody, a solution of streptavidin conjugated with one of the aforementioned enzymes is also provided. Diluting and washing buffers are provided.

Examples of detectable enzymes used in ELISAs and well known to those of skill in the art include, but are not limited, to acetylcholinesterase, alkaline phosphatase, -glycerophosphate dehydrogenase, asparaginase, β-galactosidase, β-V-steroid isomerase, catalase, glucoamylase, glucose oxidase, glucose-6-phosphate dehydrogenase, horse radish peroxidase, malate dehydrogenase, ribonuclease, staphylococcal nuclease, triose phosphateisomerase, urease and yeast alcohol dehydrogenase.

An ELISA can be used to measure mannan-binding MBL. To measure mannan-binding MBL, the microtiter wells of an ELISA plate or strip of wells are precoated with mannan as the capture molecule. Preferably, the mannan is prepared from *Saccharomyces cerevisiae* and applied at a concentration in the range of 0.1 µg/ml to 5 µg/ml, more preferably 3 µg/ml, in an appropriate coating buffer and following procedures well known to those skilled in the art. After washing the wells with a washing buffer of conventional composition, such as that containing a non-ionic detergent as blocking agent and ionized calcium, preferably at 4 mM in the form of a soluble calcium salt, the serum or heparin-anticoagulated plasma samples to be analyzed and the standards and controls, all diluted in diluting buffer containing ionized calcium (as the binding of MBL to mannan is calcium-dependent), preferably at 4 mM, are added to their respective wells. The wells are incubated at room temperature for a time period of up to one hour and are washed. A dilution of a selected monoclonal antibody of the present invention such as HYB 131-10, which has been detectably labeled with, for example, biotin, is added to each well and incubated for up to one hour. The appropriate dilution of this antibody is empirically determined and its concentration may be in the region of 1 µg/ml. The wells are washed and bound antibody is detected in accordance with well known techniques. For example, for biotinylated antibodies, a solution of streptavidin conjugated with horseradish peroxidase is added to each well and incubated for up to one hour. The wells are washed and a chromogenic substrate solution is added to each well and incubated for up to 30 minutes. Color formation is arrested by adding a strong acid to each well and the optical density of the color formed is read in a microplate reader. The amount of MBL bound to mannan in each sample well is calculated by comparing the optical density of that well with a standard curve drawn through the optical density readings for the wells containing standards derived from a gravimetrically prepared standard of purified MBL. Alternative means for detection include, but are in no way limited to, conjugation of the antibody directly with an enzyme or europium and adapting the above protocol accordingly, as is well known to those skilled in the art.

An ELISA can also be used to measure total immunoreactive MBL. To measure total immunoreactive MBL, the microtiter wells of an ELISA plate or strip of wells are precoated with a selected monoclonal antibody against MBL, such as HYB 131-10 or a similarly selected antibody as the capture molecule, applied at a concentration preferably in the range of 0.1 µg/ml to 5 µg/ml, more preferably 3 µg/ml, in an appropriate coating buffer following procedures well known to those skilled in the art. After washing the wells with a washing buffer of conventional composition well known to those skilled in the art and containing a non-ionic detergent as blocking agent, the serum or plasma samples to be analyzed and the standards and controls, all diluted in diluting buffer of conventional composition, are added to their respective wells. The wells are incubated at room temperature for a time period of up to one hour and are washed. A dilution of a different monoclonal antibody that is detectably labeled, for example, with biotin, and which may be HYB 131-11 or another antibody selected according to similar criteria, is added to each well and incubated for up to one hour. In this embodiment, at least one of the antibodies is an antibody of the present invention. The other selected antibody, however, may comprise an antibody of the present invention or HYB 131-01. The appropriate dilution of this antibody is empirically determined and its concentration may be in the region of 1 µg/ml. The wells are washed and bound antibody is detected. For biotinylated antibodies, detection is performed using a solution of streptavidin conjugated with horseradish peroxidase, which is added to each well and incubated for up to one hour. The wells are washed and a chromogenic substrate solution is added to each well and incubated for up to 30 minutes. Color formation is arrested by adding a strong acid to each well and the optical density of the color formed is read in a microplate reader. The amount of MBL in each well capable of binding simultaneously to both coating and detecting antibodies is calculated by comparing the optical density of that well with a standard curve drawn through the optical density readings for the wells containing standards derived from a gravimetrically prepared standard of purified MBL. Alternatively, antibodies can be conjugated directly with an enzyme or europium and the above protocol adapted for detection in accordance with other well known techniques.

The detection limits of the exemplified ELISA assays are in the order of 20 ng/ml in the original plasma or serum sample, if a dilution of 1/5 is used, and the upper limit of the working range can be extended to any concentration that can occur by increasing the dilution of the samples appropriately.

As will be understood by those of skill in the art upon reading this disclosure, the principles used in the above described ELISA formats can be routinely modified in accordance with well known procedures for use in other solid phase immunoassays formats. For example, in one embodiment, the capture molecule, either mannan or a monoclonal antibody against MBL is coated onto microspheres or microparticles of polystyrene or other coatable material or onto magnetic or paramagnetic beads. In another embodiment, the capture molecule is coated onto polystyrene slides. A sample is then added to the coated microparticle, bead or slide and MBL capable of binding to mannan or normal oligomerized MBL and abnormal, poorly oligomerized MBL in a sample is measured using an antibody of the present invention.

Further, as will be understood by those of skill in the art upon reading this disclosure, additional capture molecules for other analytes of interest can also be coated onto the plates, microparticles, beads or slides for the automated analysis of multiple analytes, including but not restricted to other plasma proteins such as other collectins, related proteins such as the ficolins and other animals lectins, components of the complement system, serum amyloid proteins, cytokines and peptide hormones, or indeed any analyte in the sample that can be measured by the same technical procedure using the appropriate ligands for that analyte.

Other immunoassay techniques useful with the antibodies of the present invention and well known to those of skill in the art include, but are not limited to, radioimmunoassays, techniques employing magnetic separation and electrochemiluminescent measurement applied to detection antibodies labeled, for example, with rubidium, immunoprecipitation, Western blot analysis (immunoblotting), and fluorescence-activated cell sorting (FACS). Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is also standard in the art and can be found at, for example, Ausubel, F. M. et al., *Current Protocols in Molecular Biology*, Volume 2, pp. 10.8.1–10.8.21, John Wiley & Sons, Inc., 1997.

MBL levels have been associated with increased susceptibility to and exacerbation of infections as well as autoimmune disorders and diseases. Accordingly, the methods, kits and antibodies of the present invention, which can be used to measure MBL in human plasma or serum samples that is capable of binding to mannan or both normal oligomerized MBL and abnormal, poorly oligomerized MBL are useful in diagnosing increased susceptibility to and exacerbation of infections and autoimmune diseases.

What is claimed is:

1. A kit for measuring MBL A and MBL B comprising an antibody pair comprising HYB 131-11 and HYB 131-01, wherein HYB 131-11 is a coating antibody and HYB 131-01 is a detecting antibody, or HYB 131-10 and HYB 131-11, wherein HYB 131-10 is a coating antibody and HYB 131-11 is a detecting antibody, each raised against MBL and each binding to MBL A and MBL B, said binding occurring in such a manner that when said coating antibody is bound to MBL B said detecting antibody can also bind to the MBL B and when said coating antibody is bound to MBL A said detecting antibody can also bind to the MBL A.

2. The kit of claim 1 further comprising a microtiter well plate.

3. The kit of claim 2 wherein the microtiter well plate is pre-coated with said coating antibody of the antibody pair.

4. The kit of claim 1 wherein said first detecting antibody of the antibody pair is detectably labeled.

5. The kit of claim 4 wherein said first detecting antibody is detectably labeled with biotin.

6. The kit of claim 5 further comprising a streptavidin solution conjugated with horseradish peroxidase.

7. The kit of claim 1 further comprising microspheres, microparticles of polystyrene or polystyrene slides, or magnetic or paramagnetic beads coated with said coating antibody.

* * * * *